(12) United States Patent
Geiser et al.

(10) Patent No.: US 6,972,007 B2
(45) Date of Patent: Dec. 6, 2005

(54) DEVICE FOR ADMINISTERING A PRODUCT IN DOSES

(75) Inventors: Simone Geiser, Langenthal (CH); Hanspeter Heiniger, Lotzwil (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 10/388,965

(22) Filed: Mar. 14, 2003

(65) Prior Publication Data

US 2003/0160072 A1 Aug. 28, 2003

Related U.S. Application Data

(63) Continuation of application No. PCT/CH01/00468, filed on Jul. 31, 2001.

(30) Foreign Application Priority Data

Sep. 19, 2000 (DE) ................................ 100 46 279

(51) Int. Cl.⁷ ........................... A61M 5/20; A61M 5/00
(52) U.S. Cl. ...................................... 604/211; 604/135
(58) Field of Search ............................. 604/93.01, 131, 604/134, 135, 187, 207, 208, 209, 210, 211, 604/218, 224

(56) References Cited

U.S. PATENT DOCUMENTS

| 5,112,317 | A |   | 5/1992  | Michel            |
|-----------|---|---|---------|-------------------|
| 5,611,783 | A |   | 3/1997  | Mikkelsen         |
| 5,823,998 | A | * | 10/1998 | Yamagata ............ 604/131 |
| 6,126,642 | A | * | 10/2000 | Kriesel et al. ........ 604/207 |

* cited by examiner

Primary Examiner—Nicholas D. Lucchesi
Assistant Examiner—Mark K. Han
(74) Attorney, Agent, or Firm—Dorsey & Whitney LLP

(57) ABSTRACT

A device for administering an injectable product in doses including a casing having a receptacle for a container which contains the product and accommodates a piston such that the piston can advance towards an outlet for delivering a selected product dosage, a dosing member, with which a dosing movement can be performed relative to the casing for selecting the product dosage, a drive unit, which can be coupled to the casing and the dosing member such that the drive unit can be adjusted relative to the casing from a dosing starting position to a dosing end position by the dosing movement of the dosing member, an operating mechanism which causes the drive unit to perform a delivering movement by which the piston is advanced towards the outlet, and a restoring spring, which is secured in a tensioned state and is coupled to the drive unit by a release for causing a restoring movement of the drive unit towards its dosing starting position.

19 Claims, 9 Drawing Sheets

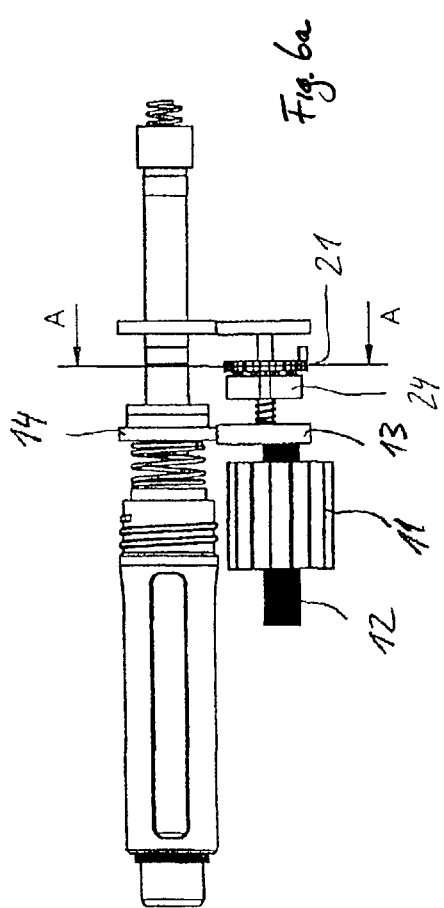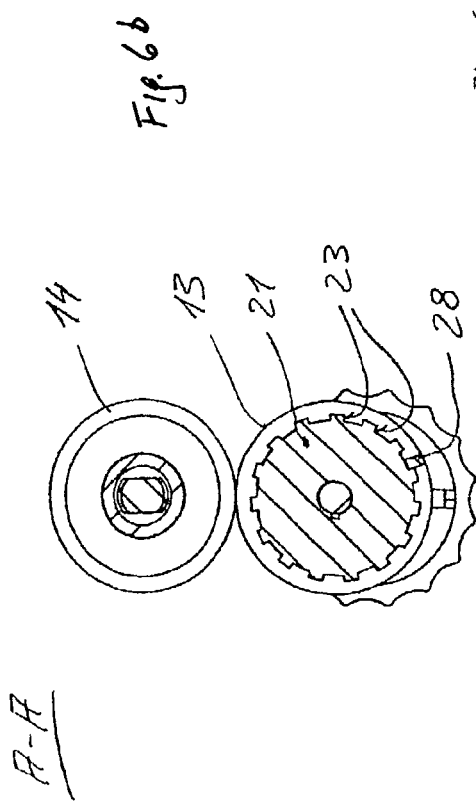
Fig. 6

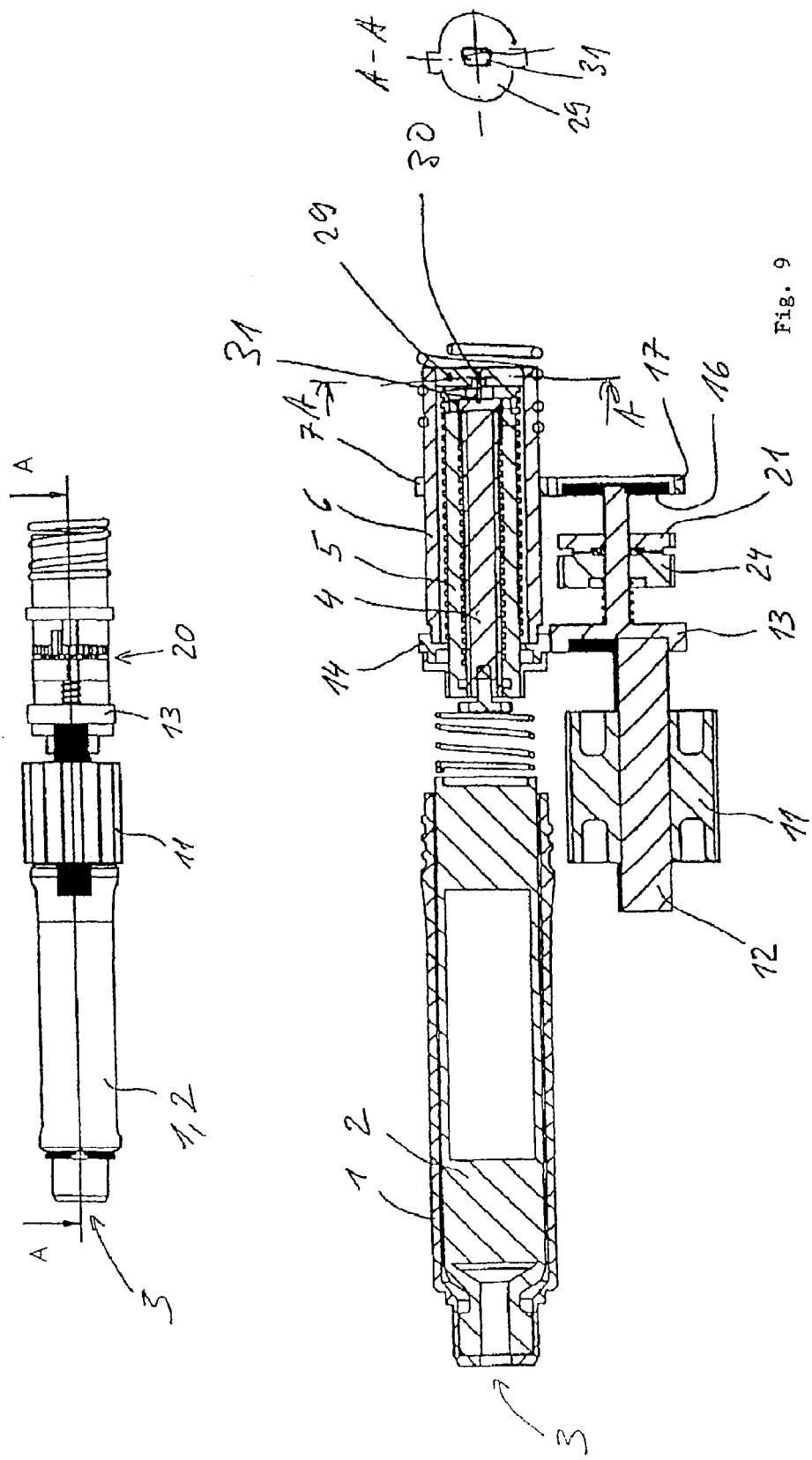

DEVICE FOR ADMINISTERING A PRODUCT IN DOSES

CROSS-REFERENCE TO RELATED APPLICATIONS

This application is a continuation of International Application PCT/CH01/00468, filed on Jul. 31, 2001, which claims priority to German Patent Application DE 100 46 279, filed on Sep. 19, 2000, the contents of which are hereby incorporated in their entirety by reference.

BACKGROUND

The invention relates to a device for administering an injectable product in doses, comprising a dosing means which can be restored or reset in accordance with a selected product dosage to be administered.

In known injection devices, for example comprising spindle drives or toothed rack drives, restoring or resetting the dosing means is either very awkward or not possible at all for a user of the device. Restoring can for example make exchanging an emptied product container easier, as is described in EP 0 614 386 B1. To this end, a toothed rack which acts on a piston arranged in the container is only provided with teeth over a portion of its perimeter. The teeth of the toothed rack cooperate with opposing teeth in such a way that it is possible to slide the toothed rack in discrete increments, for the purpose of delivering product, but the toothed rack is prevented from simply retracting. In order to restore the toothed rack, it is formed such that the teeth and the opposing teeth can be disengaged by rotating the toothed rack by 90° and the toothed rack can then be manually retracted and moved to a starting position for another dosed delivery. Restoring the driven member requires a user to perform a number of movements in coordination. When administering medically active products, a preferred use or area of application for the invention, this may be particularly difficult for users who may be suffering from fine motor disorders.

SUMMARY

It is an object of the invention to enable a device for administering an injectable product in doses to be restored or reset using as little and as simple handling as possible.

In devices such as the invention relates to, a container is accommodated in a casing, said container containing the product and accommodating a piston which can slide towards a container outlet in order to deliver a selected product dosage. A dosing member and a drive unit cooperate to select the product dosage. To select the product dosage, the dosing member performs a dosing movement relative to the casing. The drive unit is coupled to the casing and to the dosing member such that the dosing movement of the dosing member causes an adjusting movement of the drive unit from a dosing starting position to a dosing end position, relative to the casing. The device further comprises an operating means which causes the drive unit to perform a delivering movement by which the piston is advanced towards the container outlet and the selected product dosage is thereby delivered and administered.

In one embodiment, the adjusting movement of the drive unit from the dosing starting position to the dosing end position or at least towards the dosing end position is preferably a purely adjusting movement separate from the delivering movement, relative to the casing and relative to the piston. The separate adjusting movement reduces a slight gap between the piston and a driven member of the drive unit in a dosing position of the device. During the delivering movement, the driven member presses against the piston. Instead of moving the driven member relative to the piston as the adjusting movement, however, the adjusting movement can also be performed by another member of the drive unit, which performs the delivery movements together with the driven member, relative to the driven member. It is also possible for the dosing member to perform the adjusting movement, by performing an adjusting movement relative to a mechanical stopper on the casing side at the same time as its dosing movement, thus defining a stroke of the delivering movement. In this embodiment, the dosing member would also be a component of the drive unit, since it participates in the delivering movement of the drive unit. Separating the adjusting movement and the delivering movement enables the dosage to be particularly reliably selected. Furthermore, the delivering movement can always remain the same. Spindle drives in particular have proven effective for this preferred type of dosing. Although less preferred, the adjusting movement and the delivering movement can also be combined, for example if the product dosage is selected even as the delivering movement is being performed, as is possible with a drive unit formed as a toothed rack drive.

In accordance with the invention, the device comprises a restoring spring which is secured when tensioned and is coupled to the drive unit by a release. Due to the coupling, the released spring energy causes a restoring movement of the drive unit towards its dosing starting position. It is only necessary to release the safety on the restoring spring, which can be done with just one hand by simply pressing a button or sliding a slider.

In some embodiments, the device can be provided, already with a tensioned restoring spring, by a manufacturer, such that the restoring spring is only released when required. In other preferred embodiments, the restoring spring is tensioned when the drive unit is adjusted towards its dosing end position. In this case, a locking means is provided which allows the adjusting movement but prevents the drive unit from being inadvertently retracted towards its dosing starting position by the effect of the restoring spring. The restoring spring preferably acts on the drive unit via the dosing member. The locking means also preferably acts on the dosing member.

In one preferred embodiment, the restoring spring is formed by a mechanical spring, for example a spiral spring. If a member of the drive unit is rotated relative to the casing for the purpose of adjusting the drive unit, then the spiral spring can be clamped between the casing and said member of the drive unit. More preferably, such a spiral spring is clamped between the casing and the dosing member, which in this case is mounted such that it can rotate relative to the casing, in order to perform the dosing movement.

In some preferred embodiments, the drive unit is a spindle drive. A rotational movement of the dosing member is introduced into the spindle drive, and the spindle drive performs the adjusting movement. In particular, the spindle drive can be formed multi-staged, such as is described in WO 98/47552, the disclosure of which is hereby referenced and incorporated by reference with respect to advantageous spindle drives and also, more generally, with respect to advantageous, multi-stage drive units.

Advantageously, in some embodiments, the restoring spring can only be used to restore the drive unit to a dosing starting position assumed before it is first adjusted. If a spindle drive is used, then reversing the drive unit, which is often regarded as cumbrous but which is imperative for reusing the device, can be omitted.

Alternatively, an inadvertently selected overdose can be reliably corrected using the restoring spring in accordance with the invention. In some particularly preferred embodiments, the restoring spring is used both for completely restoring and partially restoring the drive unit.

The locking means cited comprises a locking member and a locking counter member which, in a mutual locking mesh, prevent the drive unit from being adjusted towards its dosing starting position, but allow it to be adjusted towards its dosing end position. The locking member is coupled to the drive unit, preferably rigidly. The locking counter member is preferably connected to the casing, secured against rotating but such that it can slide towards and away from the locking member, wherein it is loaded towards the locking member by a spring force. The locking mesh is advantageously formed by a latching connection comprising a number of latching positions which the locking member and the locking counter member can assume relative to each other. This allows the product dosage to be delivered to be selected in discrete increments.

In some preferred embodiments, to be able to correct an inadvertent overdose a release element is provided which, when operated, can release the locking mesh, engagement or connection. In order to enable the dosage to be corrected in increments, i.e., in order to be able to transfer the locking member and the locking counter member, relative to each other, from the last latching position just assumed into the last-but-one latching position assumed immediately before that, the locking member forms a mechanical stopper which cooperates with the release element. Once the locking mesh in the last latching position has been released by operating the release element, the locking member is retracted by the spring force of the restoring spring towards the last-but-one latching position. The stopper of the locking member is formed such that the stopper pushes against the release element before the locking member and the locking counter member have retracted beyond their last-but-one latching position. The release element simultaneously fulfils the tasks of releasing the locking mesh and forming a mechanical stopper to limit the reverse movement of the locking member and therefore ultimately the restoring movement of the drive unit. Since the locking member and the locking counter member are arranged in a transfer section between the restoring spring and the drive unit, the restoring spring is used not only to completely restore the drive unit but also to reduce the product dosage in increments.

In some preferred embodiments, the dosing member, the restoring spring and the locking means are arranged alongside the drive unit and preferably likewise perform the delivering movement of the drive unit. The drive unit, dosing member, restoring spring and locking means are preferably moved as a whole and do not change their positions relative to each other.

BRIEF DESCRIPTION OF THE DRAWINGS

The invention will now be described by way of describing exemplary embodiments, including preferred embodiments, with reference to the accompanying Figures.

FIG. 6, including FIGS. 6a and 6b, depicts a locking member of the locking means, in cross-section;

FIG. 9 depicts a development of the device according to FIG. 1.

DETAILED DESCRIPTION

Figure 1:
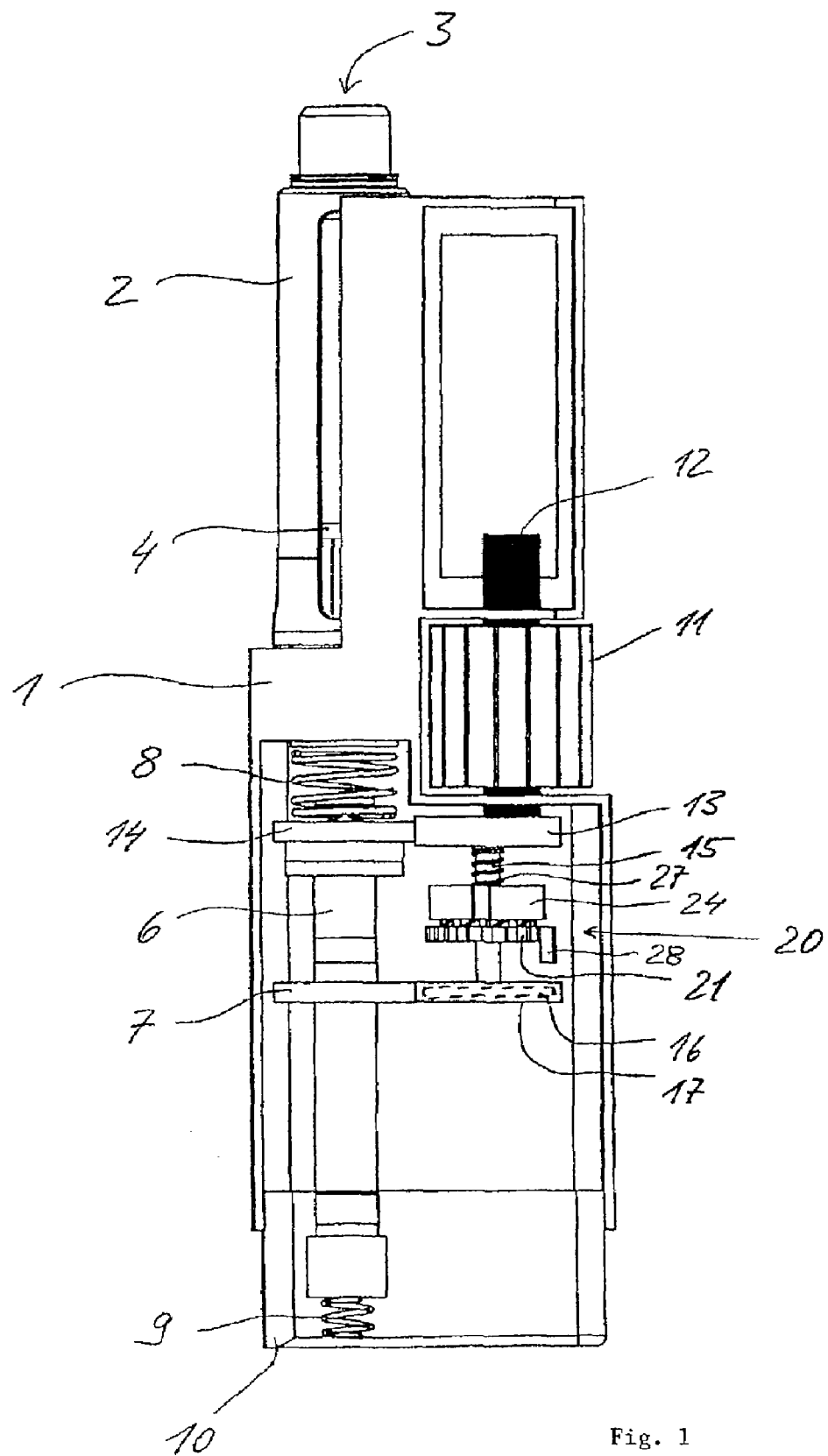
FIG. 1 depicts one embodiment of a device in accordance with the invention.

FIG. 1 shows a device for administering an injectable product in doses, which is formed as a so-called injection pen. the pen comprises a casing with a front casing portion 1 comprising a receptacle 2 for a container containing the product. The container is preferably formed by an ampoule in which a piston 35 (see FIG. 2) is arranged such that it can slide. The container is inserted into the receptacle 2 and then points via a container outlet towards a proximal outlet 3 of the receptacle 2 which faces the injection point during an injection. By advancing the piston 35 towards the outlet 3, product—for example, insulin—is displaced from the container and delivered through a connected catheter or an injection needle protruding directly from the receptacle 2, via the outlet 3. It should be understood that the needle can be of any size, including 31G, or larger or smaller than 31G.

In order to advance the piston 35 in the container towards the outlet 3, a driven member 4 is pressed against the rear side of the piston 35. The driven member fulfils the function of a piston rod and, as the product is delivered, performs the same delivering movement as the piston 35. The driven member 4 is held with other components on a rear casing portion 10 which is accommodated by the front casing portion 1 such that it can slide linearly back and forth and protrudes from the casing portion 1 via a distal end. By pressing against the distal end of the rear casing portion 10, the driven member 4 is advanced towards the outlet 3 until it initially abuts the piston 35 and as it moves further forwards, advances the piston 35 in the container. This delivering movement of the driven member 4 is limited in the proximal direction by a mechanical stopper between the front casing portion 1 and the rear casing portion 10. Due to its function, the rear casing portion 10 will also be referred to below as the operating means. During the delivering movement, a pressure spring 8 is tensioned. Once the pressure has been taken off the operating means 10, the tensioned pressure spring 8 pushes the operating means 10 together with the driven member 4 back into a distal end position again. In the distal end position, the product dosage to be delivered is selected by adjusting a slight gap between the driven member 4 and the piston 35. In adjusting the gap, i.e., dosing, the driven member 4 is moved towards the piston 35 relative to the operating means 10.

Figure 2:
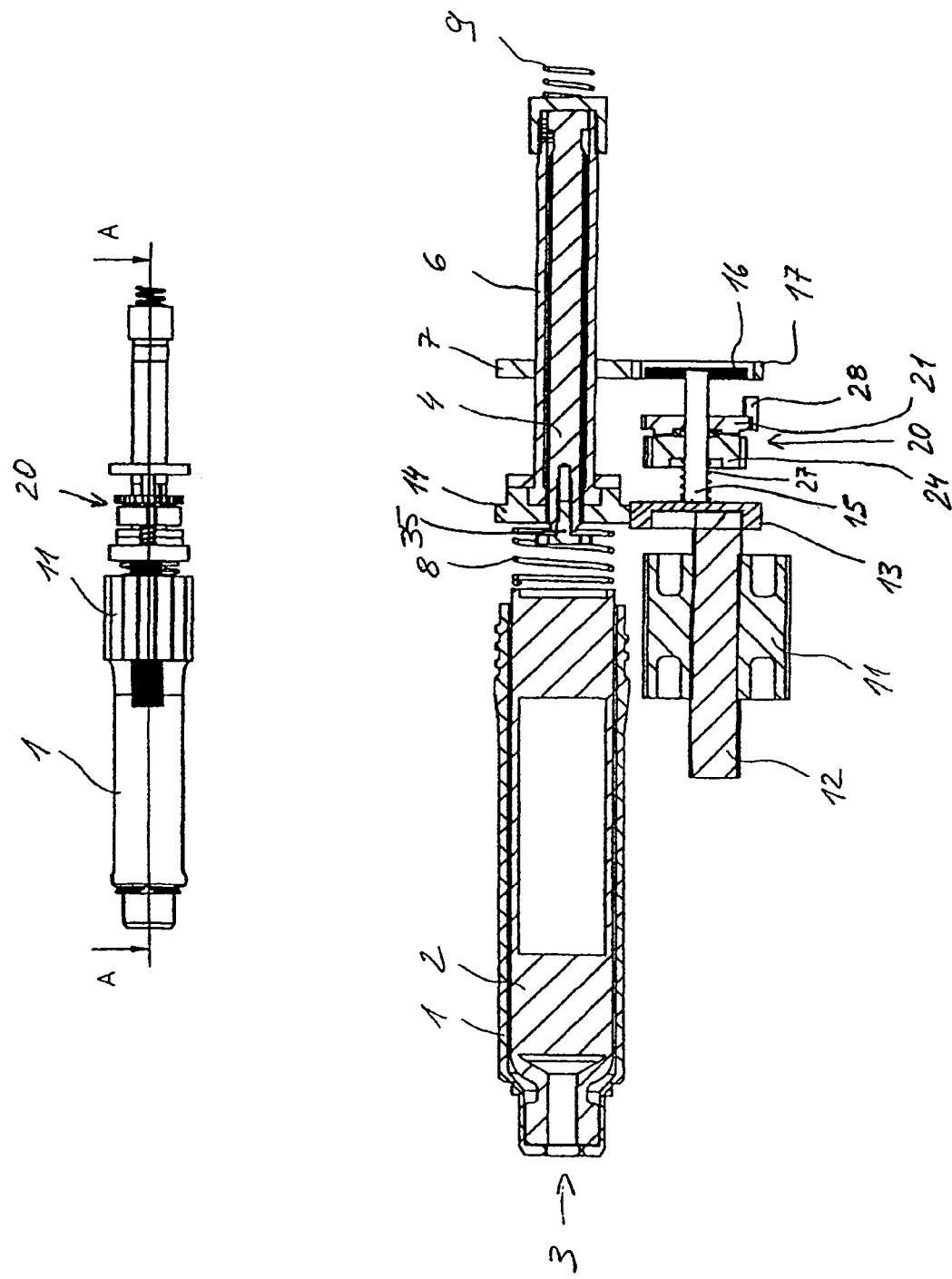
FIG. 2 depicts a portion of the device of FIG. 1, in a longitudinal section.

As may be seen in FIG. 2, the product is dosed by means of a spindle drive. The driven member 4 is the starting stage or driven stage of a drive unit formed by a spindle drive which for the purpose of dosing is single-stage. A supporting member 6 forms the supporting stage of the spindle drive. The supporting member 6 is formed by a sleeve comprising an inner thread at a proximal end. The driven member 4 is a threaded rod comprising an outer thread extending over almost the entire length. The supporting member 6 coaxially surrounds the driven member 4. The outer thread of the driven member 4 and the inner thread of the supporting member 6 engage with each other. The supporting member 6 is arranged between the pressure spring 8 and a distal equalizing spring 9. The equalizing spring 9 causes length equalization; however, the supporting member 6 pushes with its distal end against the operating means 10 during the delivering movement, such that a delivering movement of a predetermined length is performed despite the equalizing spring 9.

In one embodiment, a dosing means comprising a locking means 20 is arranged alongside the axis of the delivering movement. The dosing means comprises a dosing button 11 which may be rotated relative to the casing portions 1 and 10, about an axis parallel to the axis of the delivering movement. The user adjusts the product dosage to be delivered using the dosing button 11. A shaft 12 extends centrally through the dosing button 11 and is provided with a toothing on its outer surface. The dosing button 11 comprises an inner toothing which engages with the outer toothing of the shaft 12, such that a connection which is secured against rotating is established between the dosing button 11 and the shaft 12. However, the shaft 12 can slide back and forth relative to the dosing button 11, in the longitudinal direction of the shaft. At its distal end, the shaft 12 mates with a dosing member 13 having an inner toothing. The ratio of number of teeth between the outer toothing of the shaft 12 and the inner toothing of the dosing member 13 is 1:2. The dosing member 13 further comprises an outer toothing on its outer surface. The outer toothing of the dosing member 13 is in a mating toothed mesh or engagement with an outer toothing of another dosing member 14 which directly transfers the rotational movement to the drive unit, onto its driven member 4 in the exemplary embodiment, and is therefore referred to below as the transfer member 14.

The transfer member 14 coaxially surrounds the driven member 4. The driven member 4 extends through the transfer member 14 and is guided by the transfer member 14, such that the driven member 4 can be slid in the longitudinal direction relative to the transfer member 14 but cannot be rotated about its longitudinal axis. The transfer member 14 cannot be slid on the supporting member 6 but is fixed to it such that it can rotate about the longitudinal axis. When the transfer member 14 rotates about the common longitudinal axis of the driven member 4 and the supporting member 6, the driven member 4 is therefore rotationally slaved and, as a result of the threaded mesh with the supporting member 6, is slid in the longitudinal direction relative to the supporting member 6.

A prerequisite, however, for sliding the driven member 4 by a defined path length in the longitudinal direction relative to the supporting member 6 by rotating the transfer member 14 is that the supporting member 6 is for its part secured against being rotationally slaved. The supporting member 6 is secured against rotating by a toothed mesh with a mounting body 17 arranged alongside the supporting member 6. The mounting body 17 may be rotated relative to the casing about an axis which is parallel to the longitudinal axis of the supporting member 6. In this embodiment, the rotational axis of the mounting body 17 coincides with the rotational axis of the dosing member 13 which, while preferred, is not absolutely necessary. The mounting body 17 is secured relative to the casing in the rotational angular position assumed. The mounting body 17 is formed as a toothed wheel having an outer toothing and is in a toothed mesh with a toothed wheel 7 which surrounds the supporting member 6 and is connected to the supporting member 6, secured against rotating. By securing the mounting body 17 against rotating, and by the toothed mesh with the toothed wheel 7, the rotational block is established for the supporting member 6. While toothed surfaces are depicted, it should be appreciated that any suitable complementary engaging mechanisms, arrangements or surfaces may be used.

Figure 3:
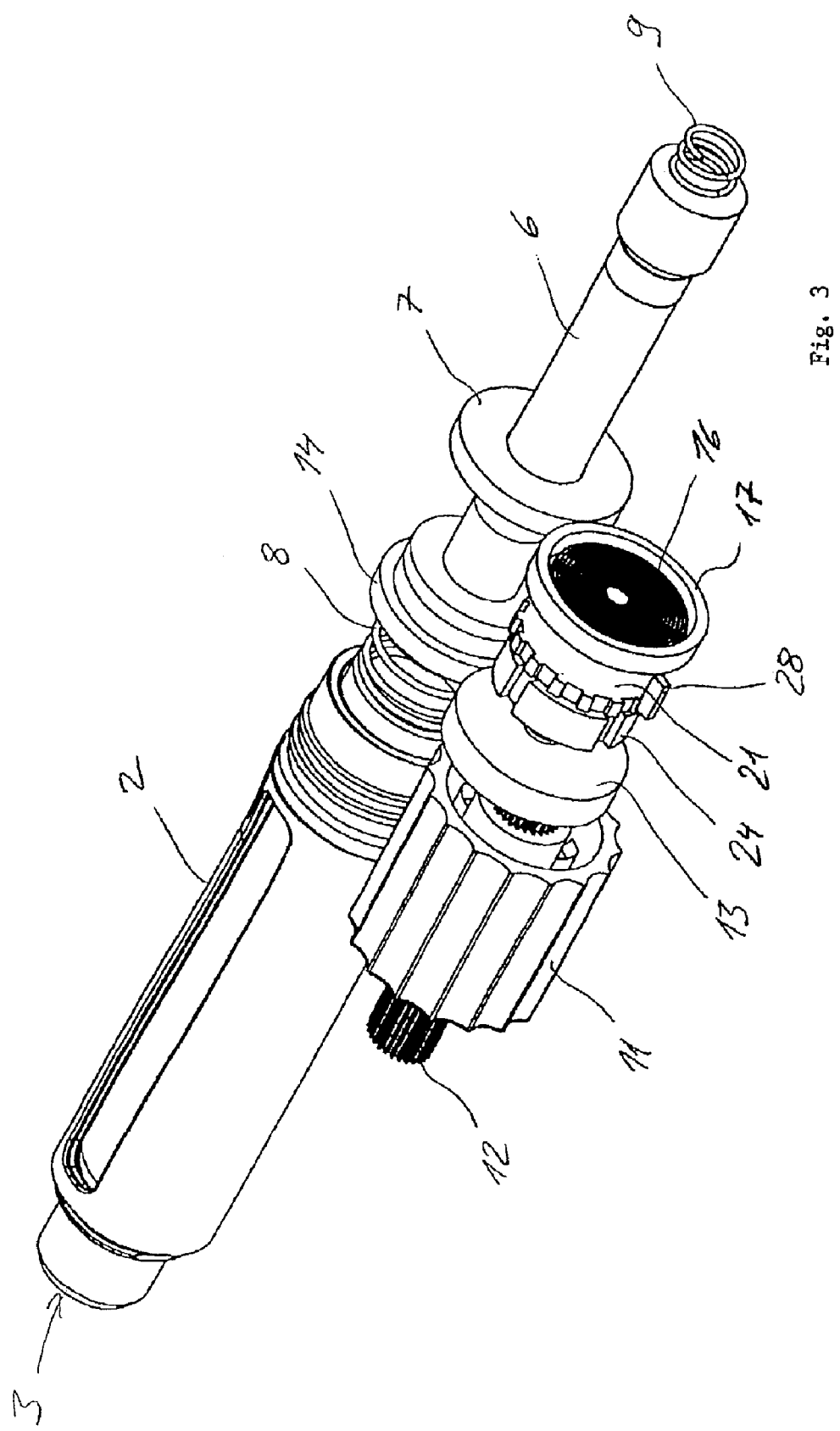
FIG. 3 depicts the portion of FIG. 2, in a perspective view.

A restoring spring 16 is supported on the mounting body 17. As may be seen more clearly in FIGS. 3 and 5, the restoring spring 16 is formed by a spiral spring comprising coils surrounding each other spirally. The spiral spring 16 is supported on the mounting body 17 via an outer spring end and on a shaft 15 via an inner spring end, said shaft 15 being connected, rotationally rigidly, to the dosing member 13. In the exemplary embodiment, the dosing member 13 and the shaft 15 are formed as one piece, the shaft 15 projecting centrically from the dosing member 13 and extending parallel to the longitudinal axis of the driven member 14, into the mounting body 17. The restoring spring 16 is wound around the distal end of the shaft 15 from its inner spring end to the outer spring end. The restoring spring 16 is thus supported on the shaft 15 and the mounting body 17 such that, when the dosing member 13 is rotated relative to the mounting body 17, the restoring spring 16 is tensioned or relaxed depending on the direction of rotation. Due to the coupling between the drive unit 4 and the dosing member 13, and the rotational block between the mounting body 17 and the supporting member 6, or more generally still the casing, the restoring spring 16 is ultimately clamped between the driven member 4 and the supporting member 6, i.e., between the members which rotate relative to each other in order to retract the driven member 4 from a dosing end position towards or up to a dosing starting position. The dosing starting position is understood here as any position of the driven member 4, relative to the piston, from which the driven member 4 is moved towards the piston during a delivering movement, without delivery actually taking place. When selecting the product dosage to be delivered, i.e., when dosing, the driven member 4 is moved from such a dosing starting position towards the piston and a slight gap between the driven member 4 and the piston is thereby reduced. The restoring spring 16 is then arranged such that it is tensioned by this adjusting movement of the drive unit and relaxed by a reverse movement towards the dosing starting position.

Figure 4:
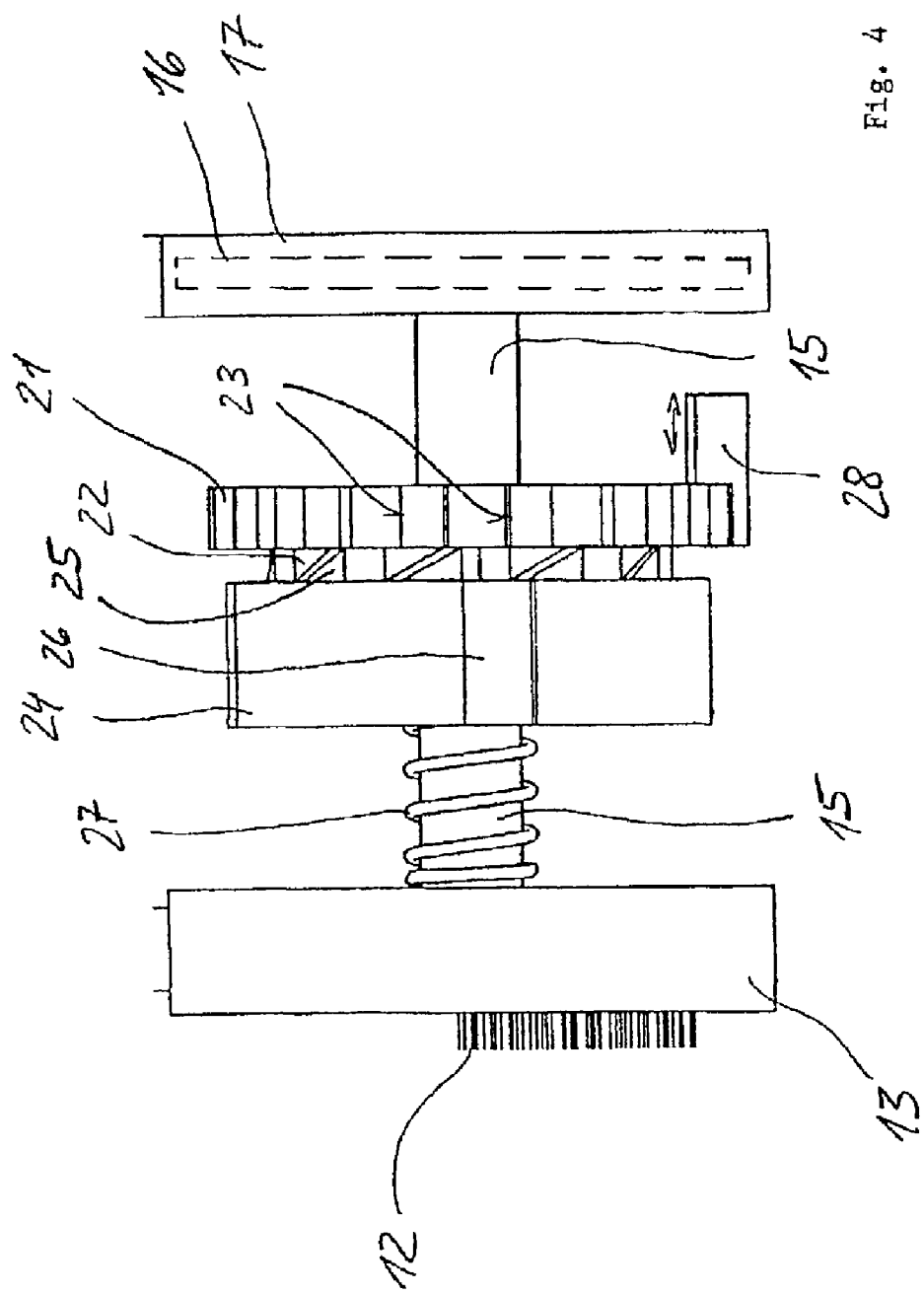
FIG. 4 depicts an embodiment of locking means for the device of the present invention.

FIG. 4 shows one embodiment of locking means 20 which is connected to the dosing member 13 in an enlarged representation. In latching positions of the locking means 20, the spring force of the tensioned restoring spring 16 is taken off the dosing member 13, and consequently off the driven member 4, by the locking means 20.

The locking means 20 comprises a locking member 21 and a locking counter member 24. The locking member 21 is a disc-shaped locking wheel which is connected to the dosing member 13, secured against rotating. In the exemplary embodiment, it is fixed to the dosing member shaft 15, secured against rotating. The locking counter member 24 is formed as an annular disc through which the dosing member shaft 15 extends. The locking counter member 24 is connected to the casing portion 10, secured against rotating, and guided relative to the casing portion 10 such that it can move back and forth along the dosing member shaft 15. Grooves 26 serves as the rotational block and linear guide and extend on the outer surface of the locking counter member 24 in the longitudinal direction and engage with the corresponding guide protrusions of the casing portion 10.

On facing sides opposite each other, the locking member 21 and the locking counter member 24 each comprise saw teeth 22 and 25 arranged in uniform distribution over a circle which is concentric with respect to the dosing member shaft 15. The saw teeth 22 of the locking member 21 and the saw teeth 25 of the locking counter member 24 are arranged such that the gradually ascending flanks of all the saw teeth 22 always simultaneously slide over the gradually ascending flanks of the saw teeth 25 when the dosing member 13 is rotated such that the drive unit is adjusted towards a dosing end position. In order to enable the sliding movement of the saw teeth 22 and 25, the locking counter member 24 can be pushed away from the locking member 21 against the restoring force of a supporting spring 27. As soon as the saw teeth 22 and 25 have slid over each other via their flat, gradually angled or ascending flanks, the locking counter member 24 snaps back forward against the locking member 21 due to the spring force of the supporting spring 27. The locking member 21 and the locking counter member 24 are prevented from rotating relative to each other in the opposite direction by the fact that the steep flanks of the saw teeth 22 and 25 oppose each other with respect to the opposing direction and the locking member 21 is thus prevented from reversing. Rotating the locking member 21 further, from one latching position to the next latching position, corresponds to a settable dosage unit.

The locking means 20 does not only serve to completely prevent the drive unit from being restored. In the event of overdosing, a dosage which has been erroneously adjusted too high can be reset again unit by unit with the aid of the locking means 20. In resetting, a release element 28 and stoppers 23 formed on the locking member 21 cooperate.

Figure 5:
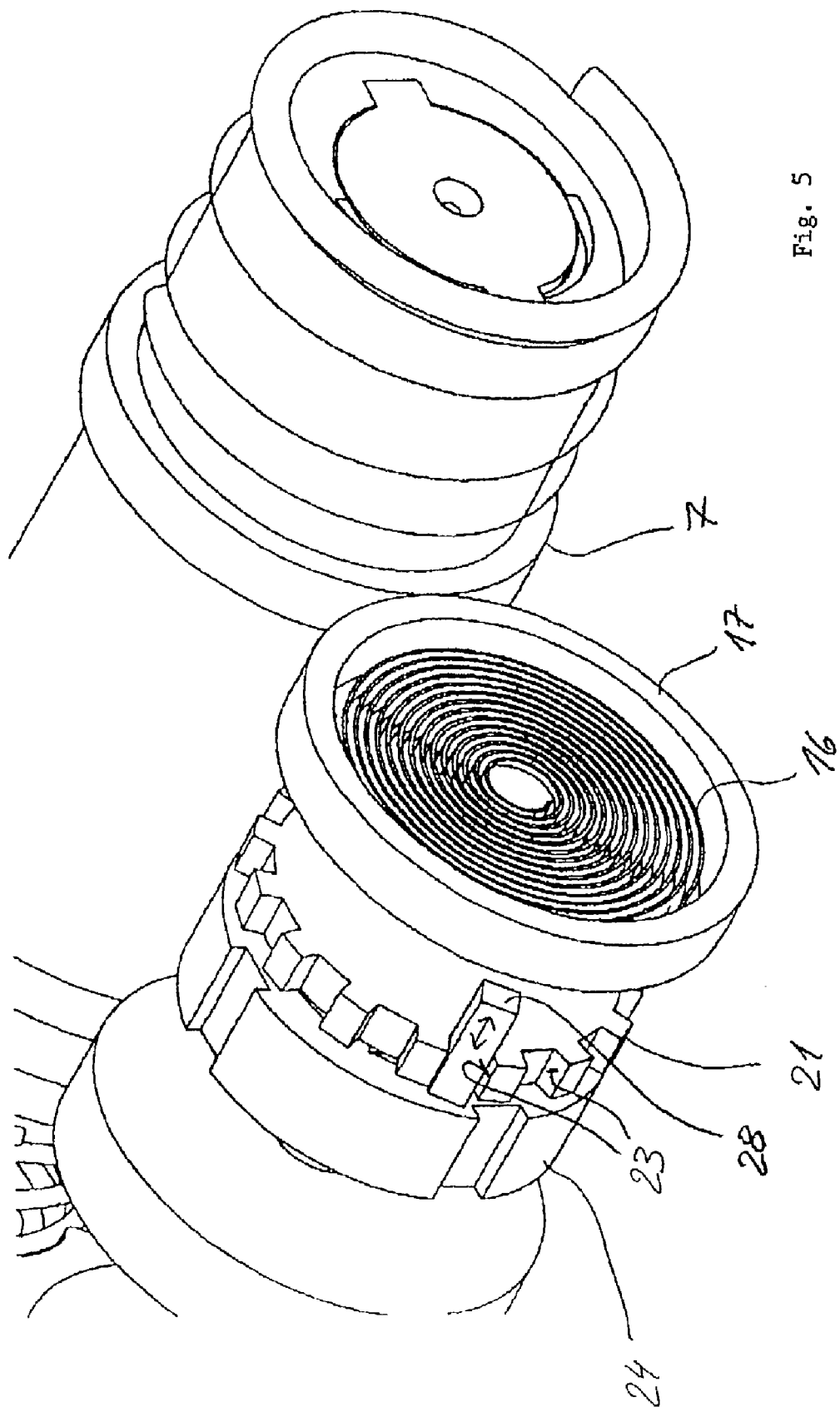
FIG. 5 depicts the locking means of FIG. 4, in a perspective view.

As may be seen from FIGS. 4 and 5 and the cross-section A—A in FIG. 6, including FIGS. 6a and 6b, the stoppers 23 are formed by a serrated rim on the outer surface of the locking member 21. The serrated rim is formed by linear grooves which are let into the outer surface area of the locking member 21 and continuously extend axially from one facing side of the locking member 21 to the other. The stoppers 23 are each formed by one of the two groove walls facing each other when viewed in the circumferential direction. The release element 28 is a slider which is arranged on the casing portion 10 such that it can be slid into the grooves of the locking member 21, towards the locking counter member 24, and slid out again from said grooves. It is inserted against a spring force, such that the release element 28 is automatically moved out of the groove mesh again once it is released. The sliding direction is indicated in FIGS. 4 and 5 by a double arrow. The release element 28 exhibits a width, measured in the circumferential direction of the locking member 21, which is smaller than the width of the grooves of the locking member 21. Once the release element 28 has been inserted into one of the grooves, a slight gap remains between the stopper 23 formed on the locking member 21 and the opposing area of the release element 28, as may best be seen in the cross-section in FIG. 6.

The functionality or operation of the device of the first embodiment is explained as follows:

As shown in FIG. 2, the drive unit assumes its first dosing starting position before a first delivery and a first dosing. A container accommodated in the receptacle 2 is still completely full. The first dosing is made from this first dosing starting position. To this end, the dosing button 11 is rotated relative to the casing (FIG. 1). By rotating the dosing button 11, the shaft 12 is rotationally slaved. The shaft 12 mates with the inner toothing of the dosing member 13. Due to the ratio of number of teeth, which may be varied, the rotational angular speed of the shaft 12 is reduced in a ratio of 2:1 when transferred to the dosing member 13. The dosing member 13 mates with the transfer member 14 in a ratio of 1:1.

When rotated, the transfer member 14 slaves the connected driven member 4, secured against rotating. The supporting member 6 is held in its rotational angular position relative to the mounting body 17 and relative to the casing due to the toothed mesh between the toothed wheel 7 and the mounting body 17 and the fact that the mounting body 17 is secured against rotating relative to the casing. As a result of the threaded mesh between the driven member 4 and the supporting member 6, the rotating driven member 4 is moved towards the outlet 3.

The rotational movement and the non-rotating connection between the dosing member 13 and the shaft 15 tensions the restoring spring 16 on the one hand and rotationally slaves the locking member 21 relative to the locking counter member 24 on the other. The saw toothed mesh and the spring movement of the locking counter member 24 back and forth enable the locking member 21 and the locking counter member 24 to rotate relative to each other. They are prevented, however, from reversing due to the saw toothed mesh. Furthermore, the saw toothed mesh generates an easily audible clicking sound which makes each increase by one dosing unit audible to the user. In addition, an optical display of the number of dosing units cumulatively selected in said dosing is preferably provided, based on electronically detecting the rotational angular position of one of the members rotated during dosing.

Once the dosage is selected, the supporting member 6 is advanced with the driven member 4, together with the other components of the dosing means including the locking means 20, relative to the casing portion 1, towards the outlet 3 up to the proximal end position of the operating means 10, by manually pressing against the operating means 10. In the course of this delivery movement, the driven member 4 initially pushes against the piston, which is advanced in the container towards the outlet 3 when the driven member 4 is advanced further. By advancing the piston, an amount of product corresponding to the dosage set is displaced from the container and delivered through the outlet 3 and a connected injection needle. As soon as the pressure is taken away from the operating means 10, the operating means 10 moves back to its distal end position again due to the pressure of the pressure spring 8. In the distal end position of the operating means 10, the driven member 4 then assumes its new dosing starting position for another dosing and product delivery. This process, i.e., dosing and subsequent delivery movement, can be repeated a number of times, until the driven member 4 has performed the delivery movement after reaching its last dosing end position and the container is, ideally, completely empty.

In one embodiment, at the end of the delivery movement, the shaft 12 pushes against a switch connected to an optical display, which resets the display to "0". The mesh between the dosing member 13 and the shaft 12 is correspondingly secured against rotating, such that the shaft 12 participates in all the sliding movements of the dosing member 13.

In order to use the device again, the driven member 4 has to be retracted from the last dosing end position, preferably up to its first dosing starting position. The restoring movement is automatically performed by means of the restoring spring 16, when the rotational block between the mounting body 17 and the rear casing portion 10 is released. To this end, a release element of its own is provided, for example, another slider which engages with the mounting body 17 to establish the rotational block and is disengaged from the mounting body 17 when the rotational block is released. Once the rotational block has been released, the mounting body 17 rotates about a rotational axis which coincides with that of the dosing member 13 due to the stored spring energy. Due to the facing mesh or engagement with the mounting body 17, the toothed wheel 7 and the supporting member 6 connected to it, secured against rotating, are necessarily rotationally slaved. The locking mesh between the locking member 21 and the locking counter member 24 secures the dosing member 13 in the rotational angular position assumed relative to the rear casing portion 10. Due to the toothed mesh, the transfer member 14 and the drive member 4 connected to it, secured against rotating, also retain their rotational angular positions assumed. Due to the relative rotation between the supporting member 6 and the driven member 4 enforced in this way, the driven member 4 is inserted into the supporting member 6 as far as its first dosing starting position. In this first dosing starting position, the restoring spring 16 is preferably biased, in order to ensure that the driven member 4 is completely retracted, even after the device has been used a number of times.

If, while dosing, i.e., during the adjusting movement of the drive unit from a dosing starting position to the next dosing end position, the user has inadvertently selected too many dosing units, this overdose can be corrected by means of the release element 28. To effect this, the release element 28 is pushed into the axially opposing groove of the locking member 21, against the pressure of a spring, and pushed further up to the locking counter member 24, until the locking counter member 24 protrudes beyond the locking member 21, against the pressure of the supporting spring 27. The release element 28 can be advanced against the locking counter member 24 until the mutually opposing steep flanks of the saw teeth 22 and 25 (FIG. 4) in the latching position assumed disengage. As soon as this locking mesh is released, the locking counter member 24 rotates counter to the direction of rotation when increasing the dosage, due to the spring force of the restoring spring 16. Reversing the locking member 21 is limited, however, by the release element 28. For the locking member 21 can only be reversed by the slight gap remaining between the release element 28 and the stopper 23 formed by the opposing groove wall. If the release element 28 is released, then it retracts again due to the spring force bearing on it and ultimately leaves the groove of the locking member 21. During this movement, the locking counter member 24 is initially pressed against the locking member 21 again by the supporting spring 27. As soon as the release element 28 has completely left the groove of the locking member 21 and the pair of stoppers 23, 28 have been released, the locking member 21 reverses further due to the spring force of the restoring spring 16, until the mutually opposing steep tooth flanks of the saw teeth 22 and 25 abut each other. Reversing the locking member 21 by operating the release element 28 corresponds to resetting by one dosing unit.

Figure 7:
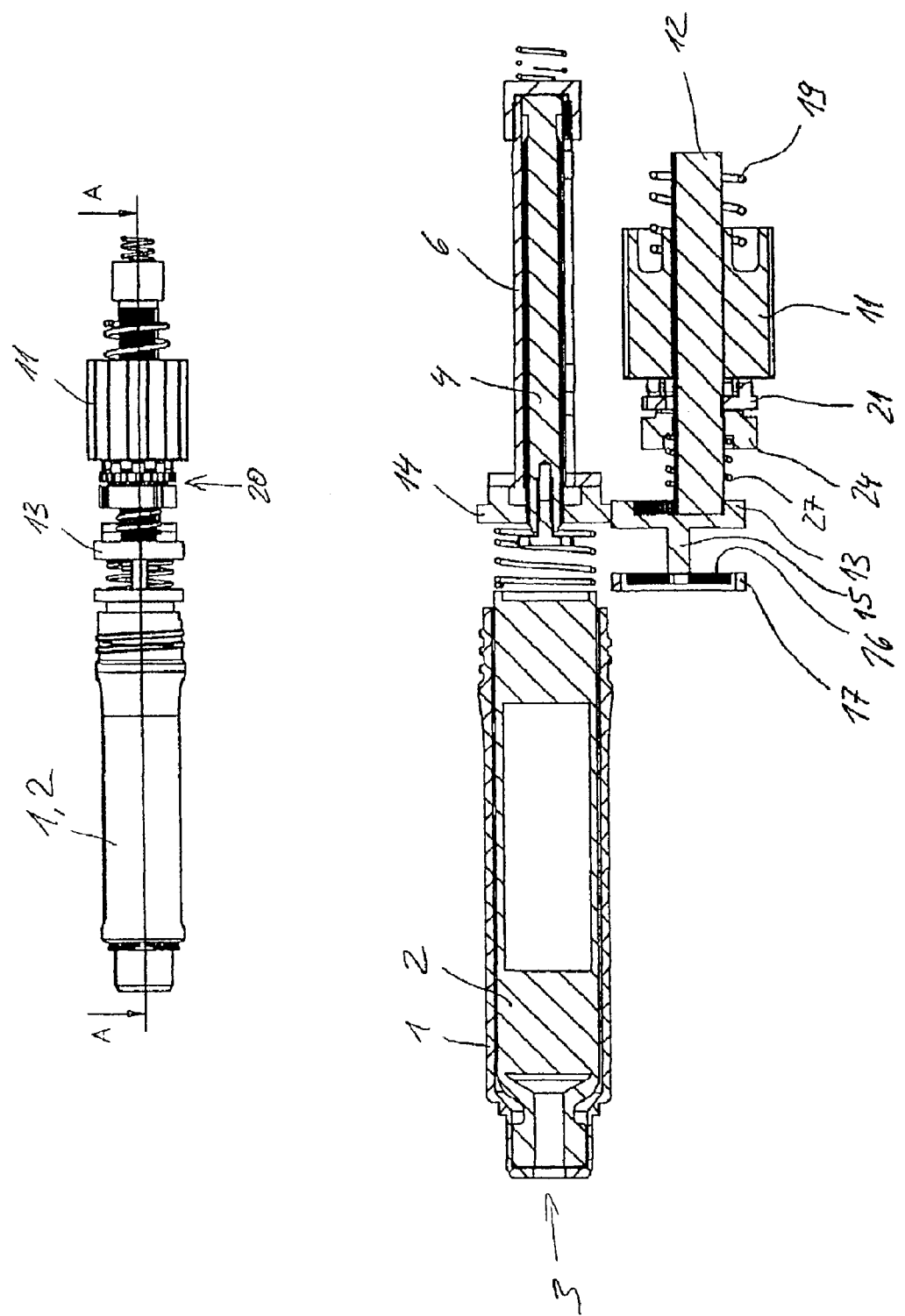
FIG. 7 depicts a second embodiment of the device in accordance with the invention.

FIG. 7 shows a longitudinal section of the parts of a device according to a second exemplary embodiment. In this embodiment, both adjusting movements of the drive unit, namely the movement of the driven member 4 towards the dosing end position and the movement towards the dosing starting position, are performed by the mesh or engagement with the dosing member 13. The mounting body 17 is simply connected, secured against rotating, to the rear casing portion 10, and only coupled to the spindle drive via the dosing member 13. The restoring spring 16 is supported via an inner spring end on a shaft or trunnion 15 which projects centrically from the dosing member 13, secured against rotating, and is connected to it. The supporting member 6 is held directly by the casing portion 1 (FIG. 1), secured against rotating. With respect to the drive unit and clamping the restoring spring 16, there are no other changes from the device of the first embodiment. In the second embodiment, the spindle drive can, however, alternatively be formed between the driven member 4 and the transfer member 14 and the supporting member 6 can serve purely as a linear guide for the driven member 4 during the adjusting movement.

The locking means 20 is not, however, arranged on a shaft connected to the dosing member 13, secured against rotating, but along the dosing shaft 12. The mesh between the shaft 12 and the dosing member 13 is, however, the same as in the device of the first embodiment.

Figure 8:
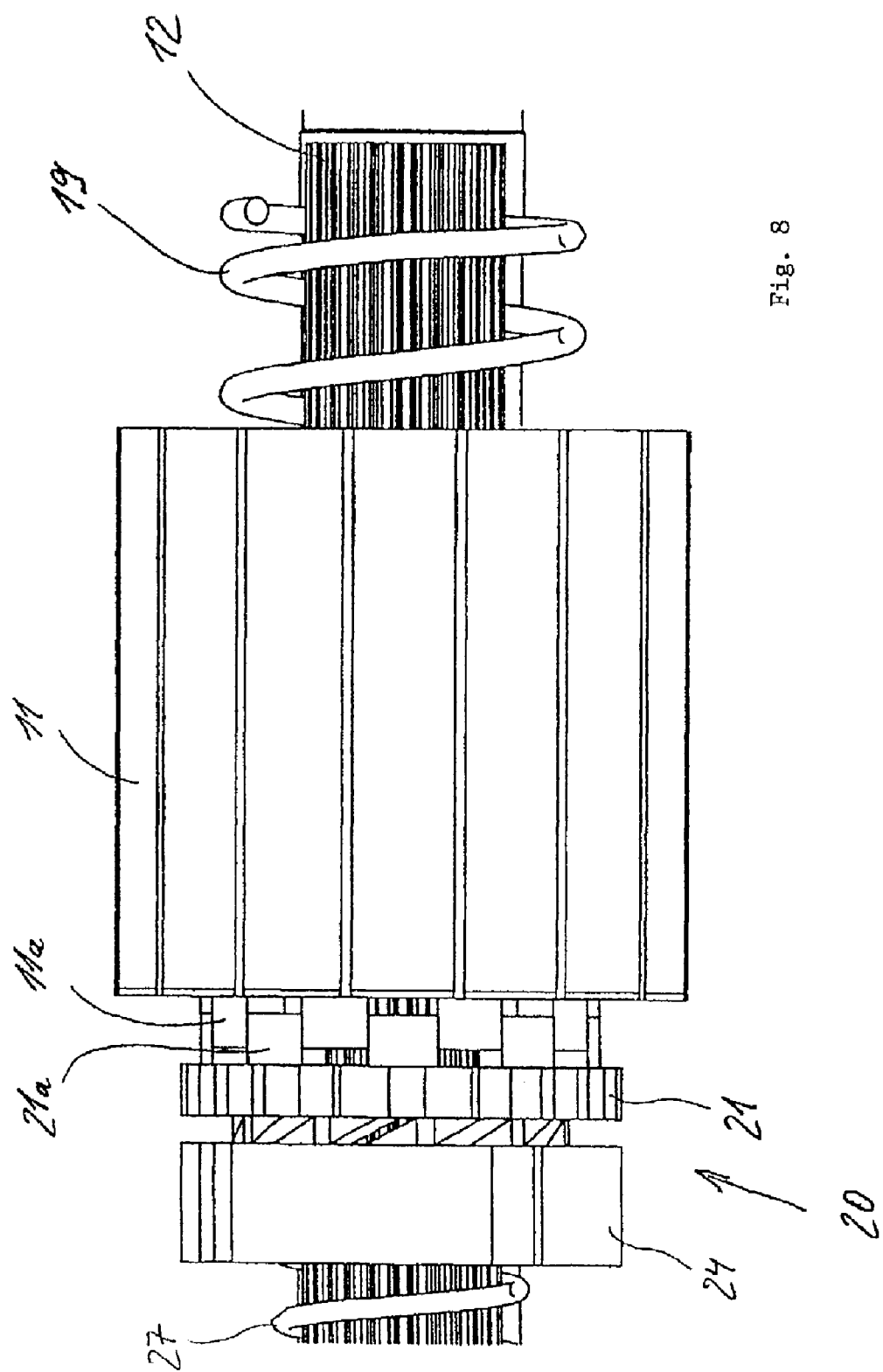
FIG. 8 depicts an embodiment of locking means for the device depicted in FIG. 7.

FIG. 8 shows one embodiment of the locking means 20 in an enlarged representation. The locking member 21 surrounds the shaft 12 and is mounted such that it can rotate relative to the shaft 12. The dosing button 11 is connected to the shaft 12, secured against rotating, as in the first embodiment. On their facing sides, which face each other, the dosing button 11 and the locking member 21 comprise a number of catches 11a and 21a which mesh with each other to form a rotational block between the dosing button 11 and the locking member 21, as shown in FIG. 8. The dosing button 11 can be moved against the force of a spring 19, away from the locking member 21, out of the rotational blocking mesh formed by the catches 11a and 21a. The locking counter member 24 is again mounted secured against rotating, but along the shaft 12 against the force of a supporting spring 27, such that it can linearly slide towards the dosing member 13. The form and functionality of the locking member 21 and the locking counter member 24 is the same as in the first embodiment, with the exception of the locking member 21 being rotationally slaved by the dosing button 11.

With respect to the functionality, too, reference may be made to the full content of the embodiments of the first embodiment, with the exception of completely restoring the drive unit to its first or most distal dosing starting position. In order to trigger the restoring movement after reaching the last dosing end position, however, the dosing button 11 is pushed away from the locking member 21, against the force of a spring 19, which releases the rotational block between the dosing button 11 and the locking member 21. Once the rotational block is released, the shaft 12, the dosing button 11 and the dosing member 13 are reversed by the spring force of the restoring spring 16. During this reversing, the driven member 4 is retracted to its most distal dosing starting position, via the mesh with the transfer member 14.

FIG. 9 shows a third embodiment which differs from the first embodiment with respect to the drive unit. The spindle drive of the drive unit of the third embodiment is two-stage, with the driven member 4 as the starting stage, a drive member 5 as an intermediate stage and the supporting member 6 as the supporting stage. During dosing, the supporting member 6 is held relative to the rear casing portion 10, secured against rotating and secured against sliding, as in the other two embodiments.

The transfer member 14, which is rotary driven by the dosing member 13, slaves the drive member 5 when it is rotated. This advances the drive member 5 relative to the supporting member 6, towards the outlet 3, via a threaded mesh with the supporting member 6. As it is translated, the drive member 5 slaves the driven member 4. In addition, the driven member 4 is advanced relative to the drive member 5, towards the outlet 3, via a threaded mesh with the drive member 5. In order to maintain the movements of the drive member 5 and the driven member 4 relative to each other and relative to the supporting member 6, a rotational block 29 in the form of a disc is fixed to the distal end of the drive member 5. It is fixed such that the drive member 5 can be rotated relative to the rotational block 29, but slaves the rotational block 29 when it is itself translated relative to the supporting member 6. The rotational block 29 is connected to the supporting member 6, secured against rotating, as for example shown in the section A—A, by meshing two protrusions with corresponding longitudinal grooves of the supporting member 6. A pin-shaped slaving means 31 is fixed to the rotational block 29, secured against rotating, for example by a screw 30. The driven member 4 engages with the slaving means 31 such that the driven member is prevented from rotating relative to the slaving means 31, though it is possible for the driven member 4 to be translated relative to the slaving means 31. The driven member 4 is thus connected to the supporting member 6, secured against rotating, via the slaving means 31 and the rotational block 29. Due to the multiple stages, comprising a number of stages 4 and 5 moved in the longitudinal direction, a spindle drive having a short design and a large dosing length is achieved.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, said device comprising:
   a) a casing comprising a receptacle for a container which contains said product and accommodates a piston, such that said piston can advance toward an outlet of the container for delivering a selected product dosage;
   b) a dosing member which can perform a dosing movement relative to said casing for selecting said product dosage, wherein a user of the device adjusts the dosing member for selecting the product dosage for each administration;
   c) a drive unit coupleable to the casing and said dosing member such that said drive unit can be adjusted relative to the casing from a dosing starting position to a dosing end position by the dosing movement of the dosing member;
   d) operating means for causing the drive unit to perform a delivering movement by which the piston is advanced toward said outlet;
   e) a restoring spring in a tensioned state coupled to the drive unit by a release whereby it can selectively cause a restoring movement of the drive unit towards its dosing starting position; and
   f) a release element configured for correcting an inadvertent overdose.

2. The device as set forth in claim 1, wherein said restoring spring is tensioned by adjusting the drive unit towards the dosing end position, and a locking means prevents the drive unit from being restored.

3. The device as set forth in claim 1, wherein the restoring spring comprises a spiral spring clamped between the casing and a rotating member which can be rotated relative to the casing, said rotating member and the restoring spring being tensioned when the drive unit is adjusted.

4. The device as set forth in claim 3, wherein the rotating member advances a driven member of the drive unit via a spindle drive towards the piston during the dosing movement.

5. The device as set forth in claim 4, wherein said spindle drive comprises a supporting member which is mounted such that it can rotate relative to the casing, but is secured against rotating, from which it can be released.

6. The device as set forth in claim 4, wherein the driven member extends through the dosing member and is guided by the dosing member such that the driven member may be slid in the longitudinal direction relative to the dosing member but may not be rotated about a longitudinal axis.

7. The device as set forth in claim 1, further comprising locking means in a locking mesh for preventing the drive unit from being restored, wherein the restoring spring is clamped between a mounting body and a rotating member, said rotating member rotated when the drive unit is adjusted, wherein said mounting body is mounted such that it can rotate relative to the casing and engages with the drive unit for rotary driving, said locking means comprising a releaseable rotational block which prevents the mounting body from rotating relative to the casing.

8. The device as set forth in claim 1, further comprising a locking member coupled to the drive unit and a locking counter member coupled to the casing, in a locking mesh, to prevent the drive unit from being restored.

9. The device as set forth in claim 8, wherein said locking member can be latched with said locking counter member in latching positions, to form said locking mesh, and a release element is provided, to release the locking mesh.

10. The device as set forth in claim 9, wherein the locking member forms a stopper which comes to rest against said release element after the locking mesh has been released, and limits the restoring movement of the drive unit.

11. The device as set forth in claim 8, wherein the locking member and the locking counter member, in the locking mesh, are pressed against each other by means of a spring.

12. The device as set forth in claim 8, wherein:
   the dosing movement of the dosing member is a rotational movement;
   a shaft is connected to the dosing member, said shaft rotating when the dosing member is rotated;
   the locking member is positioned on the shaft, secured against rotating; and
   the locking counter member can be disengaged from the locking mesh along the length of the shaft against the force of a spring.

13. The device as set forth in claim 1, wherein the dosing member is mounted such that it can rotate about a rotational axis relative to the casing and a shaft projects from the dosing member towards the rotational axis, the restoring spring being supported on said shaft.

14. The device as set forth in claim 1, further comprising a dosing button is associated with the casing such that it can rotate, said dosing button engaging a shaft such that a rotational movement of the dosing button causes a rotational movement of the shaft and the shaft can slide longitudinally relative to the dosing button, said shaft engaging the dosing member to generate the dosing movement of the dosing member.

15. The device as set forth in claim 1, wherein the dosing member and the restoring spring are arranged alongside the drive unit in the casing.

16. The device as set forth in claim 1, wherein the restoring spring is also configured to reduce the selected product dosage in increments.

17. The device as set forth in claim 1, wherein the release element is formed on a locking member.

18. A device for administering an injectable product in doses comprising:
  a casing having a receptacle for a container which contains the product and accommodates a piston such that the piston can advance towards an outlet of the container for delivering a selected product dose;
  a dosing member moveable relative to the casing for selecting the product dose, wherein a user of the device adjusts the dosing member for selecting the product dosage for each administration;
  a drive unit coupleable to the casing and the dosing member such that the drive unit can be adjusted relative to the casing from a dosing starting position to a dosing end position by moving the dosing member;
  an operating mechanism which causes the drive unit to perform a delivering movement by which the piston is advanced towards the outlet;
  a restoring spring in a tensioned state releasably coupled to the drive unit for causing a restoring movement of the drive unit toward the dosing starting position when released; and
  a release element configured for correcting an inadvertent overdose.

19. The device as set forth in claim 18, wherein the restoring spring is also configured to reduce the selected product dosage in increments.

* * * * *

UNITED STATES PATENT AND TRADEMARK OFFICE
CERTIFICATE OF CORRECTION

PATENT NO. : 6,972,007 B2
DATED : December 6, 2005
INVENTOR(S) : Simone Geiser and Hanspeter Heiniger It is certified that error appears in the above-identified patent and that said Letters Patent is hereby corrected as shown below:

<u>Title page,</u>
Item [54], Title, should read -- DEVICE FOR ADMINISTERING AN INJECTABLE PRODUCT IN DOSES --.

Signed and Sealed this

Twenty-eighth Day of March, 2006

JON W. DUDAS
*Director of the United States Patent and Trademark Office*